United States Patent [19]

Rölla

[11] Patent Number: 4,714,608

[45] Date of Patent: Dec. 22, 1987

[54] AQUEOUS DENTAL PREPARATION CONTAINING FLUORIDE IONS AND THE USE THEREOF

[76] Inventor: Gunnar Rölla, Kragsvn. 13, 0391 Oslo 3, Norway

[21] Appl. No.: 879,229

[22] Filed: Jun. 9, 1986

[30] Foreign Application Priority Data

Oct. 9, 1984 [NO] Norway .................................. 844037

[51] Int. Cl.$^4$ .............................................. A61K 7/18
[52] U.S. Cl. ..................................................... 424/52
[58] Field of Search .......................................... 424/52

[56] References Cited

FOREIGN PATENT DOCUMENTS 1572164 7/1980 United Kingdom .

OTHER PUBLICATIONS

*Accepted Dental Therapeutics*, 38th ed., American Dental Association, Chicago, Ill., 1979, p. 262.
Ogaard et al., *Caries Research*, No. 2, 1987, Abstracts from the 33rd ORCA Congress, Abst. No. 3.

*Primary Examiner*—J. R. Brown
*Assistant Examiner*—F. T. Moezie
*Attorney, Agent, or Firm*—Wenderoth, Lind & Ponack

[57] ABSTRACT

Aqueous dental preparation containing fluoride ions and having a pH of maximum about 2. The preparation is suitably based on aqueous hydrofluoric acid (HF), particularly with a concentration of 0.5–5% (w/v).

The aqueous fluoride-containing solution, particularly dilute hydrofluoric acid, having a pH of maximum about 2 for the treatment of teeth, is employed particularly by direct application, if desired, before or after the application of a solution containing calcium ions to the teeth.

10 Claims, No Drawings

AQUEOUS DENTAL PREPARATION CONTAINING FLUORIDE IONS AND THE USE THEREOF

It is known that fluorides may be used to prevent dental caries. The procedure usually involves topical applications of aqueous NaF-solutions by a dentist once or several times per year. It is usual to employ solutions which contain 2% (w/v) NaF, i.e. about 1% $F^-$. It is further known that a fluoride containing resin preparation "Duraphat", containing about 2.5% $F^-$, can be used to prevent dental caries. It has finally been suggested to use an acidulated phosphofluoride (APF) in the form of an aqueous solution which contains about 1.2% $F^-$ at a pH of 2.9. It is also known to use different fluorides in tooth paste. It has been assumed that fluoride is taken up by teeth, to become a part of and strengthen the enamel.

It has now been found that in order to improve dental health it is advantageous to use an aqueous preparation which contains fluoride ions and which has a pH of maximum 2. By treatment with this preparation fluoride reacts immediately with the dental enamel. It is not necessary for the patient to wait for 4-5 minutes with open mouth for the reaction to occur, which is necessary with presently used preparations.

By using the preparation of the present invention, a markedly higher uptake of fluoride in the enamel is experienced. A higher degree of protection against dental caries is obtained than with presently used preparations.

It is assumed that the improved effect of the preparation according to the invention is due to precipitation of $CaF_2$ as a thin homogeneous layer on the enamel, when fluoride is applied in an acidic form. This precipitation of $CaF_2$ on the teeth is very slow from neutral solutions, possibly due to lack of available calcium ions. $CaF_2$ is slightly soluble in the oral cavity and provides presumably a fluoride reservoir from which fluoride ions are released. This fluoride will then contribute to enamel remineralization (formation of F-apatite) and reduce the acid formation in dental plaque, through a well known effect on bacterial metabolism. Furthermore, if $CaF_2$ covers a major part of the enamel surface in the form of a homogeneous layer, $CaF_2$ as such may protect the tooth enamel directly, because it is known that $CaF_2$ is resistant against weak acids. As previously mentioned it has been found that treatment of teeth with acidic fluoride preparations according to the invention leads to a higher and more rapid precipitation of $CaF_2$ on enamel, cementum and dentine than is the case with the known preparations.

The preparation may be a fluoride salt, for example NaF, dissolved in a mineral acid, for example hydrochloric acid, but a simpler preparation is dilute aqueous hydrofluoric acid (HF). This will provide a solution with a suitable concentration of $F^-$ and a suitable pH. A suitable concentration area is 0.5-5% (w/v) HF; i.e. 0.5-5 g HF pr. 100 ml of solution. A pH of about 1.5 will be obtained, a pH which has been shown to be particularly suitable to increase $F^-$ uptake.

When the pH is low the dental environment will normally provide sufficient calcium ions for $CaF_2$ to form, but it is also possible to treat the teeth topically with calcium before or after the fluoride treatment to increase the precipitation of $CaF_2$ further.

By the use of scanning electron microscopy (SEM) it has been found that by the use of the preparation of the invention a continous homogeneous layer of $CaF_2$ is formed, whereas a neutral solution of $F^-$ gives coarse, large particles which only cover the enamel surface partially. APF gives a precipitate which consists of small particles which cover the main part of the enamel surface.

Clinically it has been found that treatment for 1 min. with an aqueous solution of about 2% HF gives a good caries protection. This has been shown in vivo in experiments where lose orthodontic bands have been fitted on contralateral premolars which were to be extracted. Caries forms under these bands in one month. Teeth pretreated with 2% HF showed no caries. The experiment has been performed on six different individuals. 2% neutral NaF gives little or no protection against caries in this system.

Extracted teeth were treated for 5 min. with different fluoride solutions, and the fluoride content (weight %) in the different parts of the teeth was investigated with an electronic analytical microprobe:

The results were as follows:

|  | HF 2% $F^-$ | 2% neutral NaF (1% $F^-$) | APF (1.23% $F^-$) | Duraphat 2.5% $F^-$ |
| --- | --- | --- | --- | --- |
| Cementum | 17% | 0.7% | 14% | 2% |
| Dentine | 33% | 0.7% | 15% | 1% |
| Enamel | 25% | 0.7% | 5% | 1% |

Besides being used in prophylactic treatment of the teeth against caries the preparation is particularly well suited for sealing of fissures i.e. protecting the fissures in the dental enamel against caries. Furthermore, the preparation is well suited for treatment of exposed root cementum which is vulnerable for dental caries, and where conventional methods appear to have little effect.

The preparation according to the invention gives a number of advantages as described above: An immediate effect, and an effect better than that obtained with previously known preparations. The preparation is also very inexpensive. The preparation is also useful in reducing the sensitivity of exposed tooth-necks. This is probably due to precipitation of a continuous layer of $CaF_2$ which protects the teeth against mechanical and chemical irritants.

I claim:

1. A dental preparation for topical application on teeth, containing fluoride ions in aqueous solution, having a maximum pH of about 2 and a minimum pH which is not so low as to be harmful.

2. The dental preparation according to claim 1, having a pH of about 1.5.

3. The dental preparation according to claim 1, which is based on aqueous hydrofluoric acid.

4. The dental preparation according to claim 1, which essentially consists of 0.5-5% (w/v) aqueous hydrofluoric acid.

5. A method for treating teeth to prevent carries which comprises applying to said teeth an effective amount of an aqueous, fluoride-containing solution having a maximum pH of about 2 and a minimum pH which is not so low as to be harmful, for the treatment of teeth, by direct application.

6. The method according to claim 5 wherein said solution is aqueous hydrofluoric acid having a HF concentration of 0.5–5% (w/v).

7. The method according to claim 5 which is performed before or after the application of a solution containing calcium ions to the teeth.

8. The dental preparation according to claim 2 which is based on aqueous hydrofluoric acid.

9. The dental preparation according to claim 2 which consists essentially of 0.5–5% (w/v) aqueous hydrofluoric acid.

10. The method according to claim 6 which is performed before or after the application of a solution containing calcium ions to the teeth.

* * * * *